United States Patent [19]
Dean et al.

[11] Patent Number: 6,130,207
[45] Date of Patent: *Oct. 10, 2000

[54] CELL-SPECIFIC MOLECULE AND METHOD FOR IMPORTING DNA INTO A NUCLEUS

[75] Inventors: David Andrew Dean; Warren Eugene Zimmer, both of Mobile, Ala.

[73] Assignee: South Alabama Medical Science Foundation, Mobile, Ala.

[*] Notice: This patent issued on a continued prosecution application filed under 37 CFR 1.53(d), and is subject to the twenty year patent term provisions of 35 U.S.C. 154(a)(2).

[21] Appl. No.: 08/964,700

[22] Filed: Nov. 5, 1997

[51] Int. Cl.[7] .................................................. A61K 48/00
[52] U.S. Cl. .................... 514/44; 424/93.21; 435/320.1; 435/325; 435/455; 435/458; 536/23.1; 536/24.1
[58] Field of Search ............................ 514/44; 424/93.21; 435/320.1, 455, 325, 69.1, 458; 536/23.1, 21.1; 530/350

[56] References Cited

U.S. PATENT DOCUMENTS

| | | | |
|---|---|---|---|
| 5,786,171 | 7/1998 | Lee et al. | 435/69.1 |
| 5,837,283 | 11/1998 | McDonald et al. | 424/450 |
| 5,877,020 | 3/1999 | Alitalo | 435/354 |
| 5,888,765 | 3/1999 | Patterson et al. | 435/69.1 |
| 5,916,763 | 6/1999 | Williams et al. | 435/69.1 |

FOREIGN PATENT DOCUMENTS

WO 97/34915  9/1997  WIPO.

OTHER PUBLICATIONS

Szucsik et al., Genomics 28, 154–162, 1995.
Ishii, N., et al., J Virol 68(12):8209–8216 (Dec. 1994).
Feldherr, C., et al., Exp Cell Res 213(1):164–171 (Jul. 1994).
Dean, D.A., and Kasamatsu, H., J Biol Chem 269(7):4910–4916 (Feb. 18, 1994).
Xue, Z., et al., Eur J Cell Biol 62(1):13–21 (Oct. 1993).
Feldherr, C.M., et al., Proc Natl Acad Sci USA 89(22):11002–11005 (Nov. 15, 1992).
Yoneda, Y., et al., Exp Cell Res 201(2):313–320 (Aug. 1992).
Lassner, M.W., et al., Plant Mol Biol 17(2):229–234 (Aug. 1991).
Rihs, H.P., et al., EMBO J 10(3):633–639 (Mar. 1991).
Clever, J., and Kasamatsu, H., Virology 181(1):78–90 (Mar. 1991).
Ono, T., et al., Neurosci Lett 117(3):259–263 (Sep. 18, 1990).
Gharakhanian, E., and Kasamatsu, H., Virology 178(1):62–71 (Sep. 1990).
Lobl, T.J., et al., Biopolymers 29(1):197–203 (Jan. 1990).
Wychowski, C., et al., EMBO J 5(10):2569–2576 (Oct. 1986).
Graessman, M., et al., Nucl Acids Res 17(6):6603–6612 (1989).
Dean, D.A. Abstract #313 of the Keystone Symposia on Molecular and Cellular Biology, Taos, New Mexico, Feb. 4–10, 1996.
Dean, D.A., Exp Cell Res 230:293–302 (1997).
Dowty, M.E., et al., Proc Natl Acad Sci USA 92:4572–4576 (1995).
Nigg, E.A., Nature 386:779–787 (1997).
Zimmer, W.E., et al., Abstract, Develop Biol 175:399 (1996).

*Primary Examiner*—Scott D. Priebe
*Assistant Examiner*—Dave Trong Nguyen
*Attorney, Agent, or Firm*—Braman & Rogalskyj, LLP

[57] ABSTRACT

The invention provides a cell-specific nuclear targeting molecule having a nucleic acid sequence which includes a binding site for a nuclear DNA binding protein expressed only in a specific cell type. The invention further provides a plasmid for targeting a DNA molecule into the nuclei of a specific cell type. The plasmid comprises the cell-specific nuclear targeting molecule and a DNA molecule to be targeted to the nuclei of the specific cell type. This plasmid of the subject invention can be introduced into various host cells, and the cell-specific nuclear targeting molecule will target the DNA molecule to the nuclei of the specific cell type. Thus, the invention further provides a method of targeting a DNA molecule into the nuclei of a specific cell type. The method comprises providing a plasmid (the plasmid comprising the cell-specific nuclear targeting molecule and the DNA molecule to be targeted) and introducing the plasmid into the cytoplasm of the specific cell type. In this method, the cell-specific nuclear targeting molecule targets the DNA molecule into the nuclei of the specific cell type.

17 Claims, 5 Drawing Sheets

FIG. 8

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 2294 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:1:

```
CACTAAAGGG AAACGCGAAC GAAACCACGC TTTGCAGGCA CGCTTTATTT GCTTCAACAA      60

CGAGGGCTGC ATGTTTTGCA GGGACTCCCC CCCACCCCTG CCTATCTGGT GCCCTCACAC     120

AAAGGAACGG AACCAAGCCC GTGGCCCGAG CTCCCAGCCA GGAGCCCTCA GCAGCAGCAG     180

AACGTGTGAG CGTTACCCAT ATAGGGAGGT GCAGAGGGCT GGTGGTGCAC GGGGAGCTCT     240

GCATCCCCCC GCGGCCCTCA GCCTGCAGCC CCCTCCCGCT CGTGGCACCG GGTTGGCCTC     300

GCGTGCCGTG GGGTAGCCGG GCGTTCCTGC GAGCATCCCA GGCCGGCCAG CAGGCCCTCC     360

CTGCAGCCCG GCACAGCCAT GCTCCGACAG CTGATTGGCT GCGGTGGCCG AACCTTTCCT     420

TTTTAGGCTG CATCTGCTCT GGCTCTGGCT CTGCCTCCGC GGTCCAACT TCAGCCTCCC     480

CGTGCCGAGG CTCAGCTCCA ACAGAGGGAC TGCTGCACGG TGGGACGCCC TGCATGGCTG     540

GGTGAGACCA GGGGGCTGGG GAGGGCTGGG ATGGCTCTGG CTTGGACACG GCGGGGCTCG     600

TGCGCTATGG GCAGAAGTGC TGTGGCTTTT GGCACCGTTC CCTTTCCTAT GGCTGGGATA     660

CAGCTGTCGC ATCGGCTCCG TGTGGCCGTG GTCCCCCCCC CCCCCTCCCC CGCAGCGTGG     720

GCGCAATGGA CCCGGTGGCC AACCTGCCTC CATCCCACTC CCTTCTGATT CCTTTTTCCT     780

TACGCTCTGC TGGGTTGGGT TGTTTTTTTT TTTAATTTTT TTTTTTTTTT TTGCAGCATG     840
```

```
TCATATATGG CAACCTTTTG CCTCGGTGAC CTCATGTTTG GCAGCAGGCC GGGTGACGCG      900

GGCTGGGATG AAAGCAGCTG TGGGTGTCTC GCGTGAGGCT GCGGTGCAGA GCATGCTGAG      960

ACGCACAGCT GGGACCTGGG GACACATCCA GCCCAGGGAT GGGGGGGACC GGGCAGTGCA     1020

CCGCTGTGGG ACGCTCTGAG ACCGTGCCCA CATCCTCATT GCACGATGAC AGCTCCGAGG     1080

CCACGTGGAC CTCCTGTGTC CCTTTTGGCA GTGACCCCGC AGCTCGTGGG TCCTCACTGC     1140

TGCACCCACA CCTCCGCATC CTCGCCCCGA GAATGGATCG GGATGCAGCA AAACGAAGCA     1200

GAAGCGGCGC CTGCTCGTGC CTCAGTTTCC CAGCTGCAGC CTCACTTCCC ACAACTCTCA     1260

AGTAGCAGCT CCGTGGCTTC CTCCCATCCT CAGGCTCCAG AGAGAGGCCC CAGAACGGGA     1320

TGGCTGCCCT TAAAAAGGCA CTGGGCCGAT CAGCAGGTGC TGTGCGAGGG ATGGGGGCCG     1380

ATGCCTTTGC CATGGTGGGG CATTGAGGTG TCCCCAGTGC TGCTCGGGGG CAGCAGACCT     1440

CCACCTCCCC TGGGACTGGG GCTCATCCTG CTTCCAAACC TCCTGGAGGG AAGCTGAGGG     1500

CGCACCCACC GTACAGGGCC AGGTTTGAA GGACCCACAT GGGGCTCAAC GATGAGGGGT      1560

TTGGGGTTTT GGCCAGGCTG TGTGGTGCCC AGAGGACCTT TTTGGTGTCA GGGTAAACGC     1620

AGCACTGCCA GGACTCCCGC AGCACCTTTC AGCCTTGCAC TGAATTGGGC CCATCTGCCC     1680

TGGGGGTCCC TGCCCCCAAT AACTGCAACG ATGGGAGGGA AAAAATCCCA CAGAGGGAAC     1740

CCCAGGGTGG GGATGCCGGG TCGCAGGGAT GGAGCAGCAC CTCGAGGCTG TGACGCACCG     1800

CCCATCACCT GGTGTGCAGC TGGGATGCTG AACCTCTTCC AAATCAGGAT ATGCCATGGT     1860

TCTATGACTC AGGTGCACAG CAGCCCCGGG CCATCCCTAC AGCCACCGCC TTCCTGGGCA     1920

GGGCTGTGGT CAGAGAGGAC CAAAGGCCAT CGACTGGAGT ACCTCCACCT CGCTTTTGCT     1980

GAACGTCGCT TATAAGGACT TGTGTCTCGC CTGTTTATCG AAGCATAGCA TAAAAAGGAA     2040

CAGACTCACC AATGGGATGT TGCCTCCTAA GCATAGCCCC ACGTAGATTT TTTTTTTTCC     2100

CCTTACAATA ATTTAACTGT TGCTGGGTCC TACCCATCAG TCCAAGGTCA ATTTTAATGC     2160

AATAAAACAC CTTATATGGC CATATGGCTA ACACACCATC ACTTAGCCTA TTTAGGGTCT     2220

TTGTGTAGAG AGGATCCGCC TCTGAGGTTT CGTGGGCTCG TGGTATTTAT ACCAAAGCAG     2280

ATCGGGATTC GGTC                                                      2294

(2) INFORMATION FOR SEQ ID NO:2:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CCATCCCTAC AGCCACCGCC TTCCTGGGCA GGGCTGTGGT CAGAGAGGAC CAAAGGCCAT       60

CGACTGGAGT ACCTCCACCT CGCTTTTGCT GAACGTCGCT TATAAGGACT TGTGTCTCGC      120

CTGTTTATCG AAGCATAGCA TAAAAAGGAA CAGACTCACC AATGGGATGT TGCCTCCTAA      180

GCATAGCCCC ACGTAGATTT TTTTTTTCC CCTTACAATA ATTTAACTGT TGCTGGGTCC       240

TACCCATCAG TCCAAGGTCA ATTTTAATGC AATAAAACAC CTTATATGGC CATATGGCTA      300

ACACACCATC ACTTAGCCTA TTTAGGGTCT TTGTGTAGAG AGGATCCGCC TCTGAGGTTT      360

CGTGGGCTCG TGGTATTTAT ACCAAAGCAG ATCGGGATTC GGTC                       404
```

CELL-SPECIFIC MOLECULE AND METHOD FOR IMPORTING DNA INTO A NUCLEUS

FIELD OF THE INVENTION

The subject invention is directed to a molecule and method for importing DNA into the nuclei of a specific cell type.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Despite the promise and excitement of gene therapy, it is still a long way from practice. Two major problems hindering gene therapy are that (1) gene transfers to non-dividing cells are still extremely inefficient, and (2) gene transfer to specific desired non-dividing cells within a population of other cell types is even more inefficient. Thus, any way to increase the amount of gene transfer will greatly benefit this emerging field.

Many techniques and vectors for gene therapy have been developed to target genes to cells, including replication-deficient recombinant retroviruses, adenoviruses, and adeno-associated viruses, as well as non-viral vectors such as ligand-DNA conjugates or DNA lipofection. However, most targeting techniques developed to date have only addressed the ability to internalize the DNA into the cytoplasm of the cell. It is clear that gene therapy relies on the ability of targeted genes to enter the nucleus. This is true regardless of how the DNA or RNA is targeted to the cell; once within the cytoplasm, the gene must become nuclear to be transcribed, replicated, and maintained either in an integrated or episomal state, yet there has been little attention directed toward either discovering or exploiting the mechanisms used by the cell to direct DNA to the nucleus.

Recent work has begun to address the nuclear targeting and entry of plasmid DNA. Using transformed cell lines and primary cultured cells, it has been shown that plasmid DNA is able to enter the nuclei of cells in the absence of cell division and its accompanying nuclear envelope breakdown (Dean 1997). As with all other macromolecular exchange between the cytoplasm and nucleus (for a review, see Nigg 1997), DNA nuclear entry appears to be mediated by the nuclear pore complex (Dean 1997; Dowty et al. 1995). A 366 bp sequence of DNA containing the simian virus 40 (SV40) origin of replication and early promoter has been identified that is absolutely necessary for the nuclear entry of plasmid DNA in cultured cell lines derived from monkey, rat, mouse, hamster, and human origin, as well as non-transformed primary cells from rat, chicken, and human tissues (Dean 1997). Thus, nuclear import of plasmid DNA is signal-dependent and occurs in all eukaryotic cells tested to date. This DNA nuclear localization signal has been further localized to regions within the 366 bp DNA fragment. See also PCT International Publication No. WO 97/34915, published September 25, 1997, by Dean (the contents of which are hereby incorporated by reference). These results demonstrate that transport of DNA into the nucleus is sequence-specific.

The promise and potential of gene therapy techniques to cure or to alleviate symptoms in a multitude of disorders and diseases results in a continuing need for ways to increase the amount of gene transfer to cells. Ideally, a way to increase the amount of gene transfer to a specific cell type would exist for cell-specific targeting of gene therapy.

SUMMARY OF THE INVENTION

This need is met by the cell specific nuclear targeting molecule and method of the subject invention. More particularly, the invention provides a cell-specific nuclear targeting molecule having a nucleic acid sequence which includes a binding site for a nuclear DNA binding protein expressed only in a specific cell type. The invention further provides a plasmid for targeting a DNA molecule into the nuclei of a specific cell type. The plasmid comprises the cell-specific nuclear targeting molecule and a DNA molecule to be targeted to the nuclei of the specific cell type. This plasmid of the subject invention can be introduced into a population of cells, and the cell-specific nuclear targeting molecule will target the DNA molecule to the nuclei of the specific cell type present within the population of cells.

Thus, the invention further provides a method of targeting a DNA molecule into nuclei of a specific cell type. The method comprises providing a plasmid (the plasmid comprising the cell-specific nuclear targeting molecule and the DNA molecule to be targeted) and introducing the plasmid into the cytoplasm of the specific cell type. In this method, the cell-specific nuclear targeting molecule targets the DNA molecule into the nuclei of the specific cell type.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1:
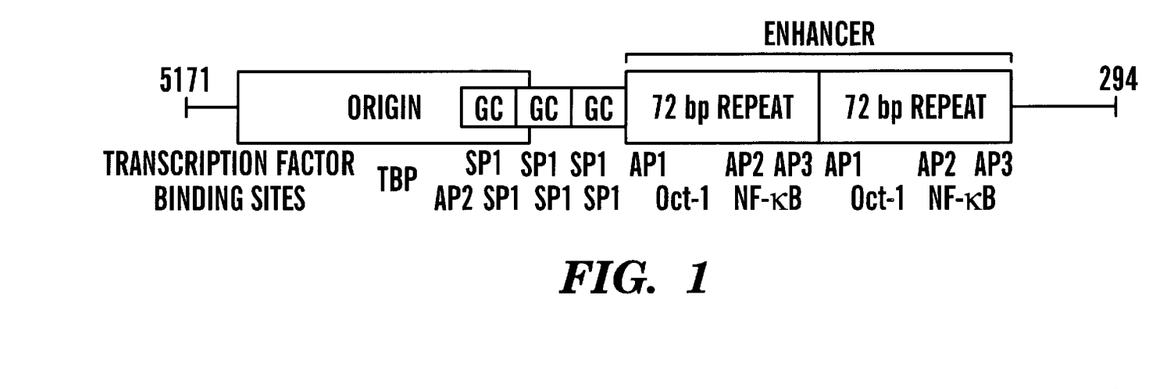
FIG. 1 shows the sequence elements and binding sites for transcription factors for a 366 bp fragment of SV40 DNA that mediates nuclear import of plasmid DNA.
Figure 2:
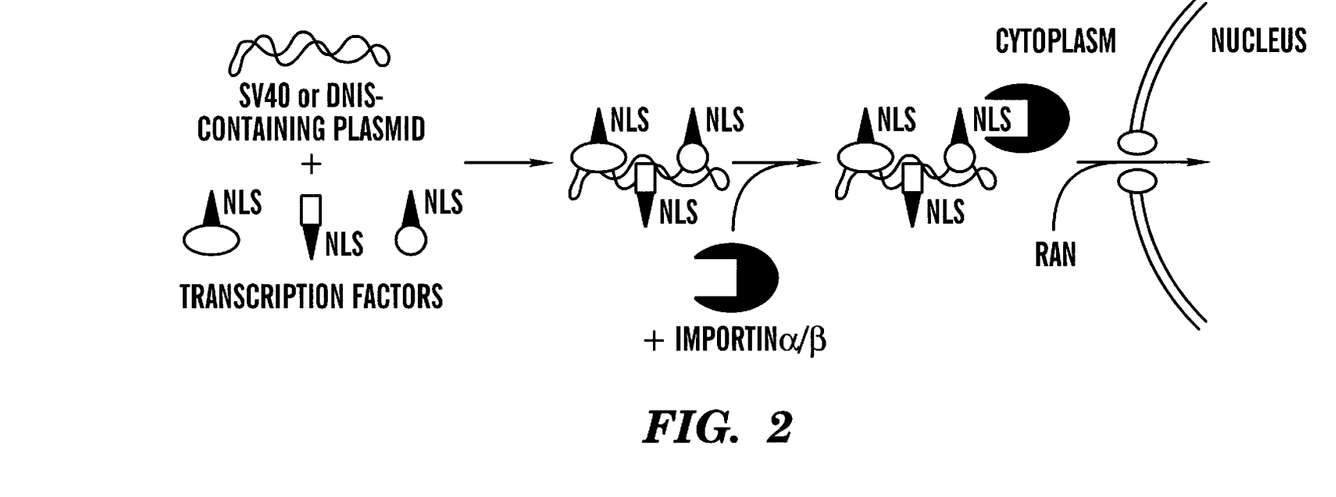
FIG. 2 illustrates a model of sequence-specific DNA nuclear import.

The invention provides a molecule and method for cell-specific nuclear import of DNA. This import is mediated by sequences containing binding sites for nuclear DNA binding proteins, such as eukaryotic transcription factors, DNA replication factors, and telomere and centromere binding proteins. Since nuclear DNA binding proteins bind to specific DNA sequences and contain or complex with nuclear localization signals (NLSs) for their nuclear import, it is likely that these proteins "coat" the DNA with NLSs, thereby allowing the DNA to utilize the NLS-mediated import machinery for nuclear entry (see model, FIG. 2). By constructing a plasmid that contains the binding site for a nuclear DNA binding protein (for example, a transcription factor) that is expressed in a specific cell type, such as a smooth muscle cell but not in any other cell type, the DNA is targeted to the nucleus only in the specific cell type (in this example, smooth muscle cells). In regard to the model in FIG. 2, the ubiquitous transcription factors such as AP1, AP4 and SP1 are replaced in the smooth muscle cell example by smooth muscle cell-specific transcription factors whose binding sites are in the piece of DNA that is targeted to the nucleus.

According to the subject invention, a plasmid has been constructed for cell-specific import into the nuclei of smooth muscle cells using DNA sequence elements from a promoter that is expressed only in smooth muscle cells. Nuclear import of DNA containing elements for this promoter occurs only in smooth muscle cells and no other cell types, including fibroblasts and epithelial cells. Based on this finding, a new generation of DNA plasmid vectors that target to specific tissues is created by identifying promoters active uniquely in those tissues, and cloning portions of the promoter containing binding sites for the unique tissue-specific transcription factors into any desired gene therapy vector. The presence of these sequences cause the vector DNA to migrate to the nucleus of non-dividing cells only in the tissue in which the promoter is active.

As used herein, "cell-specific" means that the nuclear targeting molecule targets DNA to the nuclei of the specific cell type of interest only and not to the nuclei of other cell types. The "specific cell type" refers to a "type" of cell (for example, smooth muscle cells, or skeletal muscle cells, or epithelial cells, or cancer cells, etc.).

As also used herein, "nuclear DNA binding proteins" refer to DNA binding proteins that reside in the nucleus. These nuclear, DNA binding proteins are characterized in that they bind to short DNA sequences with sequence specificity, and they are transported to the nucleus of a cell because they contain a nuclear localization signal (NLS) or because they complex with one or more other proteins that contain an NLS. These nuclear, DNA binding proteins have different functions in the regulation of DNA transcription and/or replication. Nuclear, DNA binding proteins include, for example, eukaryotic transcription factors, DNA replication factors, and telomere or centromere binding proteins. For a general discussion of nuclear, DNA binding proteins, see Nigg 1997. Table 1 gives numerous examples of tissue-specific (cell type specific) genes and some of the transcription factors responsible. These exemplified transcription factors could be used in accordance with the subject invention to target DNA to the nucleus of the specified cell. As also used herein, "transcription factors" refer to proteins that promote RNA polymerase recognition and/or initiation and/ or activation and/or repression of promoters (DNA sequences). The binding of RNA polymerase to a promoter is necessary to initiate transcription, which is the process by which the information contained in the DNA is copied into a single-stranded RNA molecule by RNA polymerase. The genetic information present in a mRNA molecule is then translated into a protein.

Preferably, the nuclear DNA binding protein is a transcription factor. In one presently preferred embodiment, the specific cell type is smooth muscle cells (SMCs), and the binding site for a nuclear DNA binding protein is within the smooth muscle gamma-actin (SMGA) promoter. In this embodiment, the cell-specific nuclear targeting molecule can have a nucleic acid sequence as shown in SEQ ID NO:1 (which is the full length SMGA promoter), or a cell-specific nuclear targeting portion thereof (such as SEQ ID NO:2, which is a 404 bp portion of the full length SMGA promoter). The entire sequence of the SMGA gene, including the SMGA promoter, is provided at GenBank Accession No. AFO12348. As used herein, a nucleic acid sequence which has a sequence as shown in a particular SEQ ID NO refers to a nucleotide sequence which is substantially the same nucleotide sequence (i.e. having at least 80 to 90% nucleotide homology and/or identity). Nucleotide additions, deletions, and/or substitutions which do not alter the functional characteristic of the molecule are encompassed by a nucleic acid sequence which is as shown in a particular SEQ ID NO, i.e., the resulting molecule is capable of cell-specific targeting of a DNA molecule to the nuclei of a specific cell type. As will be readily understood by those skilled in the art, numerous nucleotides in a SEQ ID NO are likely to be filler or spacer nucleotides which are not critical to function. n A or G which is such a filler or spacer nucleotide could thus readily be interchanged with a C or T, for example, without affecting the function of the molecule. Such nucleotides could also readily be deleted. A particular SEQ ID NO, as exemplified herein, is the SMGA promoter (or a cell-specific nuclear targeting portion thereof) which includes the binding site for a nuclear DNA binding protein. Additional nucleotides 5' or 3' to the SEQ ID NO in the SMGA promoter (or portion thereof) could be added to the SEQ ID NO without detracting from the molecule's cell-specific nuclear targeting function. Such additions, deletions, and substitutions could be made by methods known in the art, including site directed mutagenesis. The cell-specific nuclear targeting molecule as claimed herein to have a particular SEQ ID NO is intended to cover such variations which do not alter function.

The nuclear targeting molecule from the SMGA promoter is a DNA molecule, and can be isolated from cells or synthetically constructed based on the desired nucleotide sequence. As used herein, the term "isolated" when used in conjunction with the SMGA promoter refers to a nucleic acid sequence separated from the entire cell genome or from another vector which includes the desired portion of the cell genome.

The nuclear targeting molecule is most readily used by providing a plasmid (an extrachromosomal piece of DNA) for targeting a DNA molecule into a nucleus of a specific cell type. The plasmid, in its most basic form, comprises a cell-specific nuclear targeting molecule having a nucleic acid sequence which includes a binding site for a nuclear DNA binding protein expressed only in a specific cell type, and a DNA molecule to be targeted to the nuclei of the specific cell type. The structural connection of the two parts of the plasmid are that the two are contained on the same plasmid. Since the DNA molecule to be targeted need not be under expressional control of the cell-specific nuclear targeting molecule (see below), the DNA molecule does not need to be "downstream" of the cell-specific nuclear targeting molecule. As should be readily understood by those skilled in the art, "upstream" and "downstream" refer to location in the plasmid relative to the orientation of a gene (the DNA molecule to be targeted). For example, if a gene is presented in a 5' to 3' orientation, sequences to the 5' region of the gene are "upstream" and sequences to the 3' region of the gene are "downstream". In the case of a circular DNA molecule, upstream and downstream are given meaning in relation to a given gene.

The DNA molecule to be targeted to the nucleus generally encodes a protein or enzyme which would be desirable to express in the nucleus of the specific cell type, and generally is exogenous DNA (i.e., such an encoded protein or enzyme is not being expressed in the specific cell type or is being expressed at very low levels). Many examples of DNA molecules for which it would be desirable to import the molecules into a specific cell type should be readily apparent to those skilled in the art. For example, many proposed gene therapy techniques would benefit from the ability to import a DNA molecule into the nucleus according to the subject invention. In recent years, numerous examples of DNA molecules which could be imported according to the subject invention have been published. The following are examples, for illustration only, of suitable DNA molecules. Vrionis et al. 1995 disclose that the expression of herpes simplex virus thymidine kinase (HSV-tk) in a host cell may be useful in the treatment and/or prevention of brain tumors. Knowles et al. 1995 disclose that the expression of the cystic fibrosis transmembrane conductance regulator in pulmonary epithelia may be useful in the treatment and/or prevention of cystic fibrosis lung disease. Rowland et al. 1995 disclose that the expression of missing or defective proteins may be useful in the treatment and/or prevention of cardiovascular disease. Baru et al. 1995 disclose that the expression of clotting factor IX may be useful in the treatment and/or prevention of hemophilia B. Brownlee 1995 disclose that the expression of clotting factor VIII may be useful in the treatment and/or prevention of hemophilia A. Osborne et al. 1995 disclose that the expression of erythropoietin may be useful in the treatment of anemia associated with chronic renal failure, cancer, and HIV infections. Kojima et al. 1995 disclose that the expression of brain-derived neurotrophic factor may be useful in the treatment and/or prevention of neurodegenerative diseases. Betz et al. 1995 disclose that the expression of interleukin-1 receptor antagonist protein (IL-1ra) may be useful in the reduction of ischemic brain injury damage. Vaulont et al. 1995 disclose that the expression of adenosine deaminase may be useful in the treatment and/or prevention of an autosomal recessive form of severe combined immunodeficiency (SCID). Ekhterae and Stanley 1995 disclose that the expression of tissue plasminogen activator (tPA) may be useful in the enhancement of fibrinolytic activity of vascular cells. Stevenson et al. 1995 disclose that the expression of apolipoprotein E (apo E) may be useful in the treatment and/or prevention of hyperlipidemias. Phaneuf et al. 1995 disclose that the expression of fumarylacetoacetate hydrolase (FAH) may be useful in the treatment and/or prevention of type 1 hereditary tyrosinemia. Each of the above references provides a separate example of the applicability of the subject invention to nuclear importation of many different DNA molecules, for many different reasons. As should be readily apparent from the above examples, many applications of the method of the subject invention could be in the area of gene therapy, where a protein or enzyme of interest can be imported into the nuclei of the desired specific cell type.

The DNA molecule to be targeted could also express an RNA that does not code for a protein. Examples would be an "antisense oligonucleotide" that could inhibit the translation or stability of a cellular mRNA, or a stable RNA such as a tRNA, a rRNA, a UsnRNA (involved in mRNA splicing), or 7SL RNA which is part of the signal recognition particle (SRP) for protein translocation into the endoplasmic reticulum. Antisense RNAs are very popular for their potential to alter cellular mRNA levels for desired genes (Scanlon et al. 1995). Another example would be "ribozymes", RNAs that repair mutant mRNAs (Sullenger and Cech 1994).

The plasmid of the subject invention may contain other elements in addition to the cell-specific nuclear targeting molecule and the DNA molecule to be targeted. For example, it may be desirable to include a bacterial origin of replication (such as ori C for replication in *Escherichia coli*, or the origin of replication of *Bacillus subtilis* for replication therein, or the origin of replication of *Pseudomonas aeruginosa* for replication therein, etc.) so that the plasmid can be maintained and replicated in a bacterial host. Such an embodiment of the plasmid of the subject invention could also include a selection marker for selecting bacterial colonies which contain the subject plasmid. Such selection or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the plasmid to identify mammalian cells which have taken up the plasmid DNA. In the early mammalian gene transfer experiments involving viral genes, the transfer of exogenous DNA into cells was detected because the DNA had a biological activity; it led to production of infectious virus or produced stable changes in the growth properties of the transfected cells. The herpes simplex virus thymidine kinase (HSV tk) gene can be used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including:

aminoglycoside phosphotransferase (APH), using the drug G418 for selection which inhibits protein synthesis; the APH inactivates G418;

dihydrofolate reductase (DHFR):Mtx-resistant variant, using the drug methotrexate (Mtx) for selection which inhibits DHFR; the variant DHFR is resistant to Mtx;

hygromycin-B-phosphotransferase (HPH), using the drug hygromycin-B which inhibits protein synthesis; the HPH inactivates hygromycin B;

thymidine kinase (TK), using the drug aminopterin which inhibits de novo purine and thymidylate synthesis; the TK synthesizes thymidylate;

xanthine-guanine phosphoribosyltransferase (XGPRT), using the drug mycophenolic acid which inhibits de novo GMP synthesis; XGPRT synthesizes GMP from xanthine;

adenosine deaminase (ADA), using the drug 9-$\beta$-D-xylofuranosyl adenine (Xyl-A) which damages DNA; the ADA inactivates Xyl-A; and multidrug resistance (MDR), which is also known as the P-glycoprotein (Licht et al. 1995).

Gene amplification can also be used to obtain very high levels of expression of transfected genes. When cell cultures are treated with Mtx, an inhibitor of a critical metabolic enzyme, DHFR, most cells die, but eventually some Mtx-resistant cells grow up. A gene to be expressed in cells is cotransfected with a cloned dhfr gene, and the transfected cells are subjected to selection with a low concentration of Mtx. Resistant cells that have taken up the dhfr gene (and, in most cases, the cotransfected gene) multiply. Increasing the concentration of Mtx in the growth medium in small steps generates populations of cells that have progressively amplified the dhfr gene, together with linked DNA. Although this process takes several months, the resulting cell cultures capable of growing in the highest Mtx concentrations will have stably amplified the DNA encompassing the dhfr gene a hundredfold or more, leading to significant elevation of the expression of the cotransfected gene.

It may also be desirable to include, as an element of the plasmid according to the subject invention, a molecule encoding a promoter to control expression of the DNA molecule to be targeted. Such a promoter sequence would need to be positioned upstream from the DNA molecule to effectively control expression of the DNA molecule. RNA polymerase normally binds to the promoter and initiates transcription of a gene (the DNA molecule) or a group of linked genes and regulatory elements (operon). Promoters vary in their strength, i.e., ability to promote transcription. For the purpose of expressing the DNA molecule of the invention, it is desirable to use strong promoters in order to obtain a high level of transcription and, hence, expression of the gene. The promoter could also be a tissue-specific promoter which only turns on in the correct tissue, or a developmentally regulated promoter which only turns on at a certain time in the development of a cell or tissue. Examples include the alpha-actin promoter which is expressed in muscle cells (Shimizu et al. 1995), the beta globin promoter which is expressed in adult erythrocyte progenitor cells, or the gamma globin promoter which is expressed in fetal erythrocyte progenitor cells (Stamatoyannopoulos and Nienhuis 1994). Depending upon the host cell system utilized, any one of a number of suitable promoters can be used. In bacterial host cells, suitable promoters include, for example, the lac promoter, trp promoter, recA promoter, ribosomal RNA promoter, the $P_R$ and $P_L$ promoters of coliphage lambda, and others, including but not limited to, lacUV5, ompF, bla, lpp and the like, and the nos promoter. Additionally, a hybrid trp-lacUV5 (tac) promoter or other E. coli promoters produced by recombinant DNA or other synthetic DNA techniques can be used to provide for transcription of the DNA molecule of the invention. Other promoters for use in plant cells include, for example, the small subunit chlorophyll A/B binding polypeptide, the 35S promoter of cauliflower mosaic virus, and promoters isolated from plant genes, including the Pto promoter itself (Vallejos et al. 1986) to direct high levels of transcription of adjacent DNA segments. Suitable promoters for expression of genes in animal cells include, for example, the beta-actin promoter, cytomegalovirus (CMV) promoter, Adenovirus major late promoter, Thymidylate kinase (TK) promoter, and the Rous Sarcoma Virus (RSV) LTR-promoter. An example of a suitable promoter for use in insect cells is the AcMNPV polyhedrin promoter. It should be apparent that the additional promoter (to control expression of the DNA molecule to be targeted) should not be a ubiquitous promoter that includes non-cell specific binding sites for nuclear DNA binding proteins.

Bacterial host cell strains and expression vectors can be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promoter of lambda can be induced by an increase in temperature in host cells containing a temperature sensitive lambda repressor, e.g., c1857. In this way, greater than 95% of the promoter-directed transcription may be inhibited in uninduced cells. Thus, expression of the DNA molecule of the invention can be controlled.

When cloning in a eucaryotic host cell, enhancer sequences (e.g., the enhancer from the CMV immediate early promoter or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires a Shine-Dalgarno (SD) sequence about 7–9 bases 5' to the initiation codon (ATG) to provide a ribosomal binding site. Thus, any SD-ATG combination that can be utilized by host cell ribosomes can be employed. Such combinations include but are not limited to the SD-ATG combination from the CRO gene or the N gene of coliphage lambda, or from the E. coli tryptophan E, D, C, B or A genes. Additionally, any SD-ATG combination produced by recombinant DNA or other techniques involving incorporation of synthetic nucleotides can be used.

In accordance with the subject invention, the DNA of the plasmid as described herein is targeted into the nuclei of the specific cell type, where the DNA molecule to be targeted is expressed. Since the nuclear-localized plasmid DNA will eventually be degraded, it may be desirable for long term expression of the DNA molecule in the nuclei of the specific cell type to integrate the plasmid DNA into the genome of the specific cell type. In such an embodiment, the plasmid of the subject invention further includes a molecule to direct integration of the DNA molecule into the genome of the specific cell type. Such integration sequences are known in the art, and include, for example, the inverted terminal repeats of adeno-associated virus (ITRs), retroviral long terminal repeats (LTRs), and other viral sequences shown to cause incorporation or integration of the viral genome into the specific cell type genome. For integration into plant genomes, the left and right Agrobacterium T-DNA border sequences allow the integration of exogenous DNA located between the left and right T-DNA border sequences into a plant cell.

As should be readily apparent, various additional elements can be included in the plasmid of the subject invention depending upon the desired goal. For ease in constructing various embodiments of the plasmid, the basic plasmid (comprising the cell-specific nuclear targeting molecule and the DNA molecule to be targeted) can also contain a number of unique restriction enzyme sites for insertion of the additional molecules or elements. As used herein, a "unique" restriction enzyme site refers to the presence of only one cleavage site for a particular restriction endonuclease within the plasmid DNA. That particular restriction endonuclease (or restriction enzyme) will, therefore, only cleave the DNA of the plasmid at that one location or "unique" site. These unique restriction sites can be provided in the plasmid of the subject invention by including a polylinker as an element of the plasmid. As used herein, a "polylinker" refers to a sequence which contains many restriction enzyme recognition sequences that are present only once in the vector or plasmid, i.e., unique restriction sites. The plasmid of the subject invention may also contain restriction sites that occur twice in close proximity (i.e., the flanking sites of the polylinker) and these could also be used to clone in sequence between the sites.

Having constructed the plasmid according to the subject invention, a host cell comprising the plasmid is also provided by the subject invention. As indicated above, for maintenance and propagation of the plasmid, a bacterial host cell (such as *Escherichia coli*) may be used. Bacterial host cells for maintenance and propagation offer the advantages of being easy to work with and capable of rapid reproduction and therefore propagation of the plasmid.

In use however, the DNA molecule to be targeted to the nucleus of a specific cell type is most likely to express a product useful in animal (including, for example, mammals, birds, amphibians, reptiles and fish), plant, yeast, or insect host cells. Suitable host cells are any cells into which a DNA molecule is desired to be introduced. For example, and referring to the many possible uses of the subject invention discussed above, the host cell may be a pulmonary epithelial cell where gene therapy of cystic fibrosis lung disease is being treated and/or prevented. Vascular cells may be a suitable host cell where tPA is desired to be expressed. Plant cells, such as of various crop plants including potato, tomato, cereals, etc., may be suitable host cells where plant disease resistance genes are desired to be expressed. Yeast cells, such as *Saccharomyces cerevisiae*, may be suitable host cells for applicability of the invention to industrial fermentation processes. In a particular insect cell, it may be desirable to express an insecticide resistance gene in order to select for that insect after exposing an environment to the insecticide. Many other suitable host cells should be readily apparent, as the invention has broad applicability to various host cells and various DNA molecules to be imported into the nucleus thereof. The importation of DNA into the nucleus of a host cell may also be desirable in vitro, using various cells lines known in the art, such as, for example, the mammalian cells identified as NIH3T3 cells, Hela cells, COS cells, and CHO cells, and the insect cell lines identified as Drosophila Schneider, Drosophila $K_c$, and Sf9.

A viral vector may provide the means for introducing the plasmid into the host cell. For example, the plasmid may be introduced into an adenovirus, retrovirus, adeno-associated virus, vaccinia virus, papovavirus, or herpes simplex virus vector and these viral vectors can then infect a mammalian cell in order to get the plasmid DNA into the cytoplasm and/or nucleus of the mammalian cell. Other mammalian viruses could similarly be used. The plasmid could also be introduced into an insect virus, such as baculovirus, for introduction into an insect cell, or a plant virus for introduction into a plant cell.

The nuclear targeting molecule of the subject invention also offers the advantage of being able to target a DNA molecule to the nucleus of a non-dividing host cell. Non-dividing cells include two classes of cells: those that are not dividing (quiescent) and those that cannot divide (i.e., many terminally differentiated cell types). When cells leave mitosis and are finished dividing, they enter the G1 phase of the cell cycle and then come to a halt at G0 (G zero). At this point they are "growth-arrested"; protein synthesis is decreased as is transcription. Upon stimulation, most cells will exit G0 and continue on with the cell cycle, leading to division. However, many cells will remain in this G0 state for a long time. Human liver cells, in the absence of liver damage, will divide only once or twice a year while gut epithelia will divide twice a day. The period of quiescence for each type of cell is different, but if it is greater than a week, the method of the subject invention is especially applicable.

An example of quiescent cells are hematopoeitic stem cells (CD34+ cells). These cells have the potential to divide and self-renew, but they are normally quiescent until stimulated to divide. These cells are a desired target for gene therapy (sickle cell disease, thalasemia, SCID), and the subject method provides a method to get DNA into the cells even though they normally do not divide. Other quiescent cells include fibroblasts in the absence of tissue damage, liver cells in the absence of liver damage, and skeletal muscle cells (these are classic "post-mitotic cells"). Non-dividing, terminally-differentiated cells are sometimes called "Permanent cells". Many cells are produced during embryogenesis in numbers that will suffice for the lifetime of the organism. Thus, once they divide and differentiate, they will never divide again. These terminally-differentiated or permanent cells include most neurons and nerve cells; non-dividing differentiated epithelial cells (i.e., top layers of skin that are still living or villus cells of the gut lumen); muscle cells of the heart; auditory hair cells of the ear; and lens cells of the eye.

For a general discussion of non-dividing cells, including quiescent and terminally differentiated cells, see Porth 1994. Additional references describing these types of cells are Seshadri and Campisi 1989 (fibroblasts); Ponchio et al. 1995 and Young et al. 1996 (hematopoietic cells); Langan and Slater 1991 (astroglia); Datta 1995 (neuroblasts); Allen et al. 1995 (skeletal muscle); and Vick et al. 1992 (oligodendrocytes).

Having thus described the cell-specific nuclear targeting molecule and plasmid according to the subject invention, as well as suitable host cells into which the plasmid can be introduced, the invention further provides a method of targeting a DNA molecule into the nuclei of a specific cell type. The method comprises first providing a plasmid according to the subject invention, and then introducing the plasmid into the cytoplasm of the specific cell type (see above for description of the plasmid and the specific cell type). The cell-specific nuclear targeting molecule which is an element of the plasmid targets the DNA molecule which is another element of the plasmid to the nuclei of the specific cell type.

Various methods are known in the art for introducing nucleic acid molecules into host cells (including the specific cell type). One method is microinjection, in which DNA is injected directly into the cytoplasm of cells through fine glass needles. Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high levels. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, retrovirus, and adeno-associated virus (AAV) (Berns and Giraud 1995).

As indicated, the method of the subject invention requires the use of a plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in procaryotic and eucaryotic cells. The DNA sequences are cloned into the plasmid vector using standard cloning procedures known in the art, as described by Sambrook et al. (1989).

If the plasmid is to be introduced into plant cells, the methods of introduction may differ slightly. The plasmid can be introduced into *Agrobacterium tumefaciens*. This introduction can be accomplished using methods known to those in the art, including electroporation, or particle bombardment. Another method that can be used to introduce the plasmid into *Agrobacterium tumefaciens* is triparental mating. In a triparental mating, the *Escherichia coli* containing the plasmid, a second *Escherichia coli* containing a helper plasmid, and an Agrobacterium are combined, resulting in introduction of the plasmid DNA into the Agrobacterium. The Agrobacterium cells are then screened using a selection marker for the presence of the plasmid DNA therein. Those cells containing the plasmid DNA are then used for further experiments.

The plasmid can also be introduced into a plant cell. One method for introduction of the plasmid into a plant cell is Agrobacterium-mediated transformation of the plant cell (stable or transient). Briefly, the tissue of plants is contacted with an inoculum of the Agrobacterium transformed with the plasmid (with exogenous DNA therein). Generally, this procedure involves inoculating the plant tissue with a suspension of the bacteria and incubating the tissue for 48 to 72 hours on regeneration medium without antibiotics at 25–280 C.

In practice, the method of Agrobacterium-mediated transformation can involve a three-step process. The plasmid DNA is first analyzed in an *Escherichia coli* host cell, and is then introduced into an *Agrobacterium tumefaciens* host cell, which is then used for Agrobacterium-mediated transfer of the T-DNA within the plasmid to the plant cell. Generally, only a portion of the T-DNA border sequences and DNA located therebetween is transferred into the plant cell by such Agrobacterium-mediated transfer. Therefore, any exogenous DNA for transfer into the plant cell should be located within the plasmid between the T-DNA border sequences.

The leaf disk technique can be utilized in conjunction with Agrobacterium-mediated transformation. Briefly, wounded plant cells (such as leaves, roots and stems) are cultured briefly with Agrobacterium cells to initiate transfer of the T-DNA from the Agrobacterium to the plant cell. After several days, the plant tissue is transferred to shoot-inducing media that contains a selective agent. After shoots are formed, the shoots are transferred to a medium that stimulates root formation.

Another method for introduction of the plasmid into a plant cell is by transformation of the plant cell cytoplasm, such as by particle bombardment.

A further method for introduction of the plasmid into a plant cell is by transformation of plant cell protoplasts (stable or transient). Plant protoplasts are enclosed only by a plasma membrane and will therefore take up macromolecules like exogenous DNA. These engineered protoplasts can be capable of regenerating whole plants. Suitable methods for introducing exogenous DNA into plant cell protoplasts include electroporation and polyethylene glycol (PEG) transformation.

An additional method for introduction of the plasmid into a plant cell is by transformation of plant organelles (such as chloroplast or mitochondria), such as by particle bombardment. Although the plasmid will not replicate in the plant organelles, the exogenous DNA may be incorporated into the genome by recombination.

As used throughout this application, electroporation is a transformation method in which, generally, a high concentration of plasmid DNA (containing exogenous DNA) is added to a suspension of host cell protoplasts, yeast, animal cells, or bacterial cells and the mixture shocked with an electrical field of 200 to 600 V/cm. Following electroporation, transformed cells are identified by growth on appropriate medium containing a selective agent.

As also used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle. Biologically active particles (e.g., dried bacterial cells containing the plasmid and exogenous DNA) can also be propelled into plant cells.

To summarize, it has been shown that plasmid DNA containing the chicken smooth muscle γ-actin (SMGA) promoter is selectively transported into the nuclei of differentiated smooth muscle cells; transport does not occur in any other cell type. Import occurs through the nuclear pore complex in the absence of mitosis, and is sequence-specific (Dean 1997). A model has been developed in which import is mediated by sequences containing binding sites for eukaryotic transcription factors. Since transcription and replication factors bind to specific DNA sequences and contain nuclear localization signals (NLSs) for their nuclear import, these proteins "coat" the DNA with NLSs, thereby allowing the DNA to utilize the NLS-mediated import machinery for nuclear entry. Moreover, the cell-selective nuclear import of the SMGA promoter is mediated by transcription factors that are expressed exclusively in smooth muscle cells. These results are the first demonstration of cell-specific nuclear import of plasmid DNA and allow the creation of new vascular gene therapy vectors that are both cell-specific and capable of greater gene transfer efficiencies.

Based on the DNA sequences that are required for the nuclear import of plasmid DNA, a model for the import reaction (FIG. 2) has been proposed. In the case of general nuclear import, the DNA fragment that gave the best transport activity contained the 72 bp enhancer repeat of the SV40 early promoter, a region rich in consensus binding sites for numerous transcription factors. These include AP1, AP2, AP3, AP4, NF-kB, Oct-1, and SP1. Since transcription factors, like all proteins, are translated in the cytoplasm, they must target to the nucleus either after synthesis or upon proper stimulation. To enter the nucleus they must either contain nuclear localization signals (NLSs) or form oligomers with other proteins that contain an NLS. Since transcription factors bind to specific DNA sequences, if DNA containing the appropriate sequences is present in the cytoplasm, it can be complexed by these proteins, thus coating the DNA with protein NLSs. The NLSs present in this nucleoprotein complex can then interact with the normal importin/karyopherin NLS receptor and enter the nucleus by the normal nuclear protein import machinery (Dean and Kasamatsu 1994).

Based on these findings, a new class of gene therapy vectors can be made that localize to the nuclei of any desired cell type by incorporating sequences that contain binding sites for transcription factors that are expressed uniquely in the desired cells. Examples include incorporating a promoter or portions thereof that contain consensus binding sites for Pax-6, a homeodomain transcription factor whose expression is limited to the developing brain and the eye (Walther and Gruss 1991; Mansouri et al. 1994) or AP-2β, a transcription factor expressed preferentially in the adult eye, kidney and skin (Moser et al. 1995) into a vector to cause its specific nuclear import in cells of the eye. Alternatively, sequences from the skeletal muscle alpha-actin promoter, which expresses only in striated muscle cells (Shimizu et al. 1995), can be incorporated into a plasmid to create a vector that only targets to the nuclei of skeletal muscle cells. For specific nuclear targeting in hematopoietic stem cells, portions of the promoter immediately upstream of the β-globin gene which contain binding sites for GATA-1 and other transcription factors that only are found in hematopoietic cells (Orlic et al. 1992) can be incorporated into the new vector. Thus, any of a number of combinations can be made which lead to greatly improved gene therapy vectors that can (1) target to the nuclei of cells in the absence of cell division, and (2) do so in a cell-specific manner. An added advantage of this approach is that the use of vectors containing these type of cell-specific DNA targeting sequences will ensure safety since nuclear import and resulting gene expression will occur only in target cells.

Materials and Methods

Plasmids.

SV40 DNA was purified from infected TC7 cells by Hirt lysis as described (Hirt 1967). The SV40 origin sequence (SV40 nts 5171 to 37) was excised from plasmid pOR1, a derivative of pBR322 (DeLucia et al. 1986), by digesting with EcoRI and HindIII and replaced with a multiple cloning site (HindIII-XbaI-NcoI-SmaI-KpnI-EcoRI) to create pDD201 and to facilitate cloing. (The numbering of SV40 nucleotides is according to convention (Tooze 1980)). pORD1 was constructed by subcloning the 366 bp HindIII-KpnI fragment from SV40 (nts 5171 to 294) containing the origin and promoter region into the plasmid pDD201.

The promoter for the smooth muscle gamma actin (SMGA) gene was obtained from a genomic clone of the chicken SMGA gene (Zimmer et al. 1996). Briefly, a chicken genomic library was constructed in EMBL-3 phage and was screened for SMGA clones using the [$^{32}$P]dCTP labeled full length cDNA, SMGA 15-1, as a probe (Kovacs and Zimmer 1993). Two clones that hybridized under high stringency were obtained. Restriction and hybridization analyses of both clones using SMGA 15-1 sequences in combination with the cDNA derived from the SMGA 3' isotype specifc probe (Kovacs and Zimmer 1993) localized transcribed sequences and revealed that the 3' end of the gene was missing in the two genomic clones, which were named SMGA6-1Z and SMGA12-1Z. A DNA fragment spanning the missing genomic sequence was obtained by PCR amplification and ligated to the existing 3' end of the SMGA6-1Z clone, to generate a complete genomic clone. A unique XbaI restriction site was introduced at position +25 in exon 1 of the SMGA gene by PCR to facilitate cloning. The full length promoter was subcloned into the pCAT-Basic vector (Promega, Madison, Wis.) using the EcoRI and XbaI sites. This plasmid was named pCAT-2294. Using an existing SmaI restriction site within the promoter, a truncated SMGA promoter containing only the 404 bp immediately upstream of the start codon was also cloned into the pCAT-Basic vector to create pCAT-404. A similar series of transcription reporter plasmids (pGL-2294 and pGL-404) were created in pGL3-basic (Promega) that express luciferase.

pCAT-Control contains the SV40 early promoter (nts 5171-130) and enhancer (nts 130-270) and was purchased from Promega.

Plasmid DNA was purified by either alkaline lysis and subsequent CsCl gradient centrifugation or Qiagen midiprep columns (San Diego, Calif.). DNA purified in either manner displayed the same intracellular distribution after cytoplasmic microinjection.

Cell culture and microinjection.

CVI cells, a subline of African Green monkey kidney epithelium, were grown on coverslips in DMEM containing 10% fetal bovine serum and cytoplasmically microinjected as described (Dean et al. 1995). Human pulmonary artery intimal and medial smooth muscle cells were a generous gift from Dr. Paul Babal (Department of Pathology, University of South Alabama, Mobile, Ala.) and were grown in DMEM containing 10% fetal bovine serum. Primary chicken gizzard smooth muscle cell cultures were established based on the method of Cambell et al. (Cambell et al. 1974). Cells were grown on collagen type IV-coated, etched coverslips in medium 199 supplemented with 20% fetal bovine serum, 1 μM insulin, 2 mM L-glutamine, and 100 units/ml of penicillin/streptomycin. At confluency, cells were differentiated by switching the culture medium to DMEM/F12 supplemented with 2 mM L-glutamine, 1 μM insulin, 100 units/ml of penicillin/streptomycin, 5 units/ml apotransferrin, and 0.2 mM ascorbic acid. Cells were maintained in this medium for 48 hours prior to microinjection. Chicken embryo fibroblasts were established as described (Hayward and Schwartz 1986).

Purified protein-free DNA was suspended in phosphate-buffered saline and injected at a concentration of 0.5 mg/ml. Assuming that 0.1 pl is delivered by microinjection (Graessman and Graessman 1986), this corresponds to approximately 8,000 molecules of plasmid injected per cell. In situ hybridization and indirect immunofluorescence.

In situ hybridizations were performed as described (Dean 1997). After microinjection and incubation for the appropriate time, the cells were permeabilized with 0.5% Triton X-100 in phosphate-buffered saline at 23° C. for 1 minute, fixed in acetone:methanol (1:1) at −20° C. for 5 minutes, and incubated in 70% formamide in 2× SSC at 70° C. for 2 minutes to denature the DNA. The cells were then hybridized overnight at 37° C. with a fluorescently-labeled probe. All samples were treated with RNaseH (8 U/ml) after hybridization and the subsequent washing steps, and the cells were mounted with DAPI and the anti-bleaching reagent DABCO. Fluorescently-labeled probes were prepared by nick translation of pBR322, pCAT-Basic, and SV40 DNA as described (Johnson et al. 1991) except that fluorescein-12-dUTP or Texas Red 5-dUTP (Molecular Probes, Eugene, Oreg.) were incorporated directly into the DNA. All photographs were taken with an Olympus BMAX50 epifluorescence microscope equipped with a PM20 photodocumentation system on 400 ASA Kodak Ektachrome or TriX-PAN film. Confocal microscopy was performed on an ACAS 570 laser-scanning confocal microscope.

EXAMPLE I

Smooth muscle-specific gene expression of the gamma-actin gene.

Figure 3:
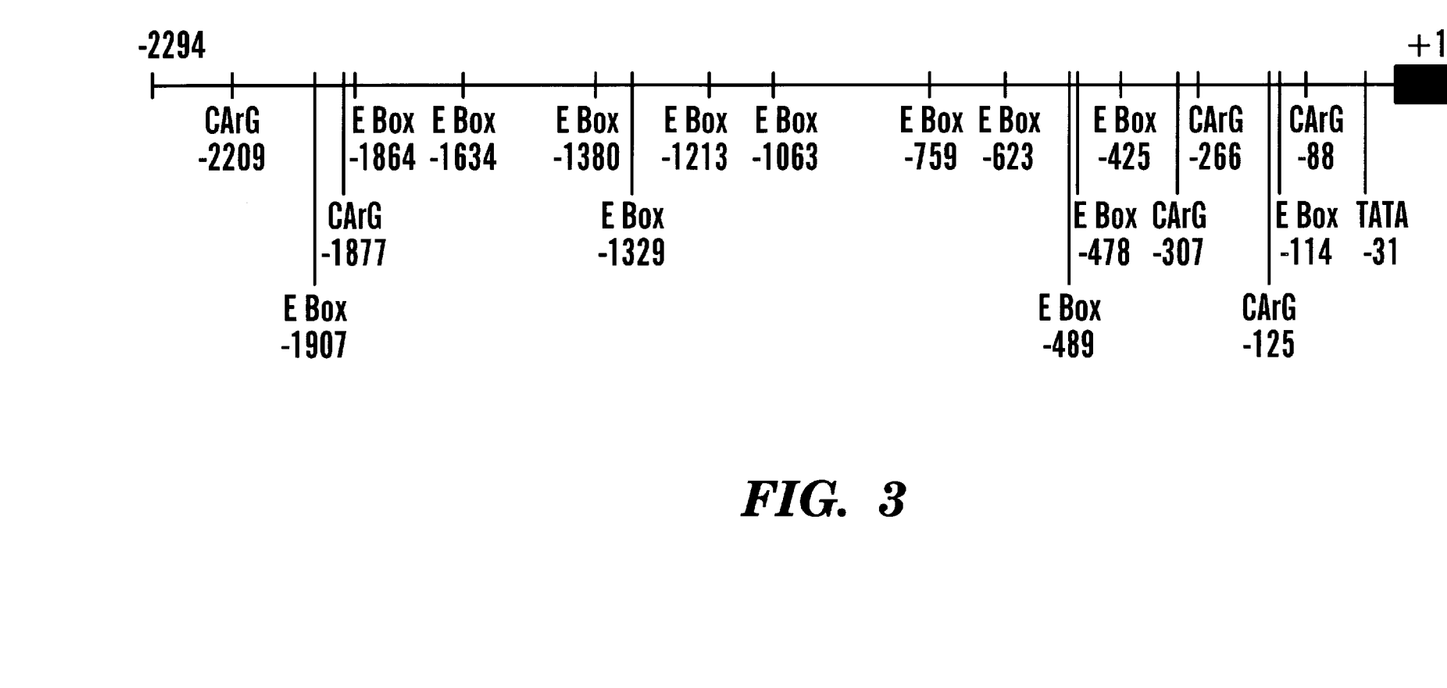
FIG. 3 shows the location of the SMGA promoter elements.

The smooth muscle gamma-actin (SMGA) gene was used to confirm that DNA nuclear import could be made cell specific. SMGA is an actin isoform that is expressed only in visceral and vascular SMCs (Zimmer et al. 1996; Kovacs and Zimmer 1993). When a reporter plasmid expressing either a luciferase or CAT gene driven by the SMGA promoter was transfected into cells, expression from the SMGA promoter was observed in human as well as chicken vascular and visceral smooth muscle cells, but not fibroblasts, endothelial cells, or epithelial cells (Zimmer et al. 1996). This selective expression is transcriptional and depends on the presence of multiple positive and negative DNA elements that interact with combinations of ubiquitous and cell type-specific transcription factors (Zimmer et al. 1996). As in the vascular smooth muscle alpha-actin gene (Shimizu et al. 1995) and the promoters of all smooth muscle genes examined to date (Kallmeier et al. 1995; Herring and Smith 1996; Li et al. 1996; Samaha et al. 1996), two cis elements are needed for smooth muscle cell-specific expression, the CArG/SRE motif and the E-Box. The avian SMGA gene promoter contains 6 CArG/SRE motifs (FIG. 3), four of which are known to be conserved in structure and location within the human (Miwa et al. 1991) and mouse SMGA genes (Szucsick and Lessard 1995). These motifs bind to serum response factor (SRF), a highly conserved protein that is developmentally regulated in smooth muscle myogenesis and which binds to DNA as a heterodimer with multiple distinct partners (Zimmer et al. 1996; Treisman 1994). The promoter also contains 13 E-box motifs, the DNA sequence that can bind members of the bHLH family of transcription factors, exemplified by the muscle-specific factor MyoD.

Because transcription factors mediate the nuclear import of plasmid DNA, the SMGA promoter is active only in differentiated smooth muscle cells and the SV40 promoter is active in all cell types (since its transcription is driven by a set of ubiquitously expressed transcription factors). Indeed, the SMGA gene is expressed preferentially in visceral and vascular smooth muscle, and tissue specific gene regulation occurs at the level of transcription (Kovacs and Zimmer 1993; Zimmer et al. 1996; Miwa et al. 1991).

Figure 4:
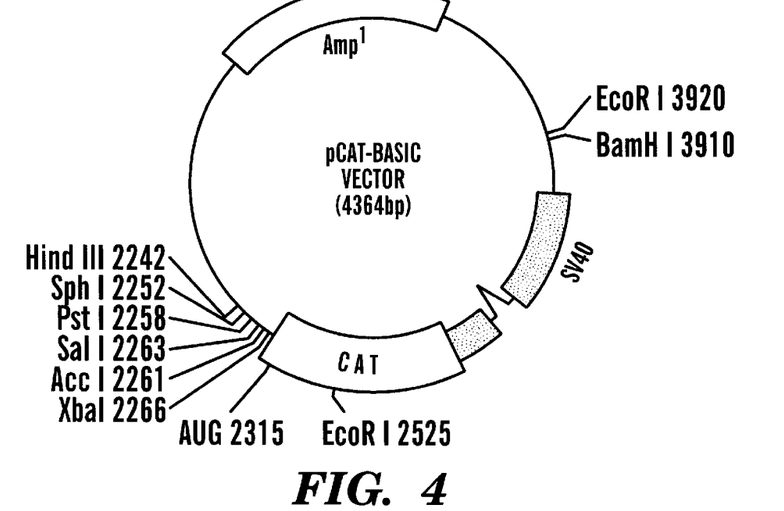
FIG. 4 is a map of the plasmid pCAT-Basic.
Figure 5:
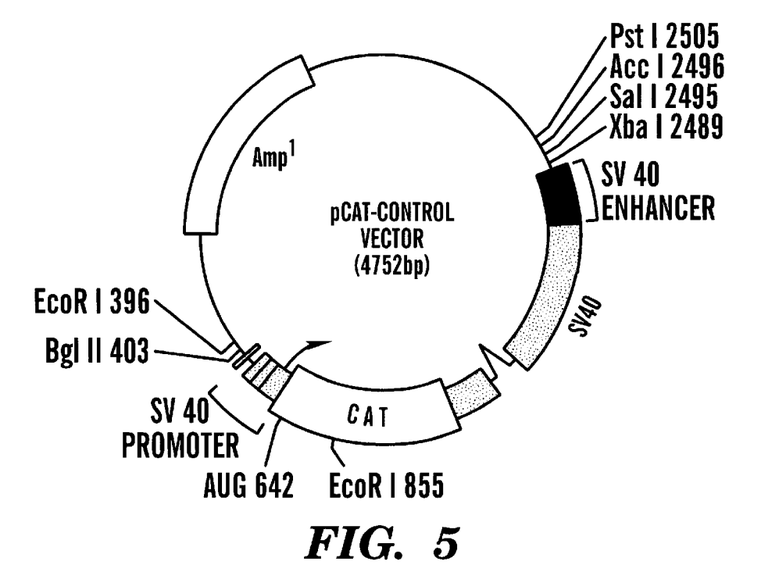
FIG. 5 is a map of the plasmid pCAT-Control.
Figure 6:
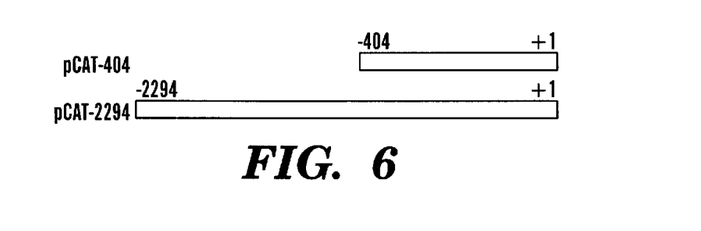
FIG. 6 shows the portions of the SMGA promoter used to construct pCAT-404 and pCAT-2294.
Figure 7:
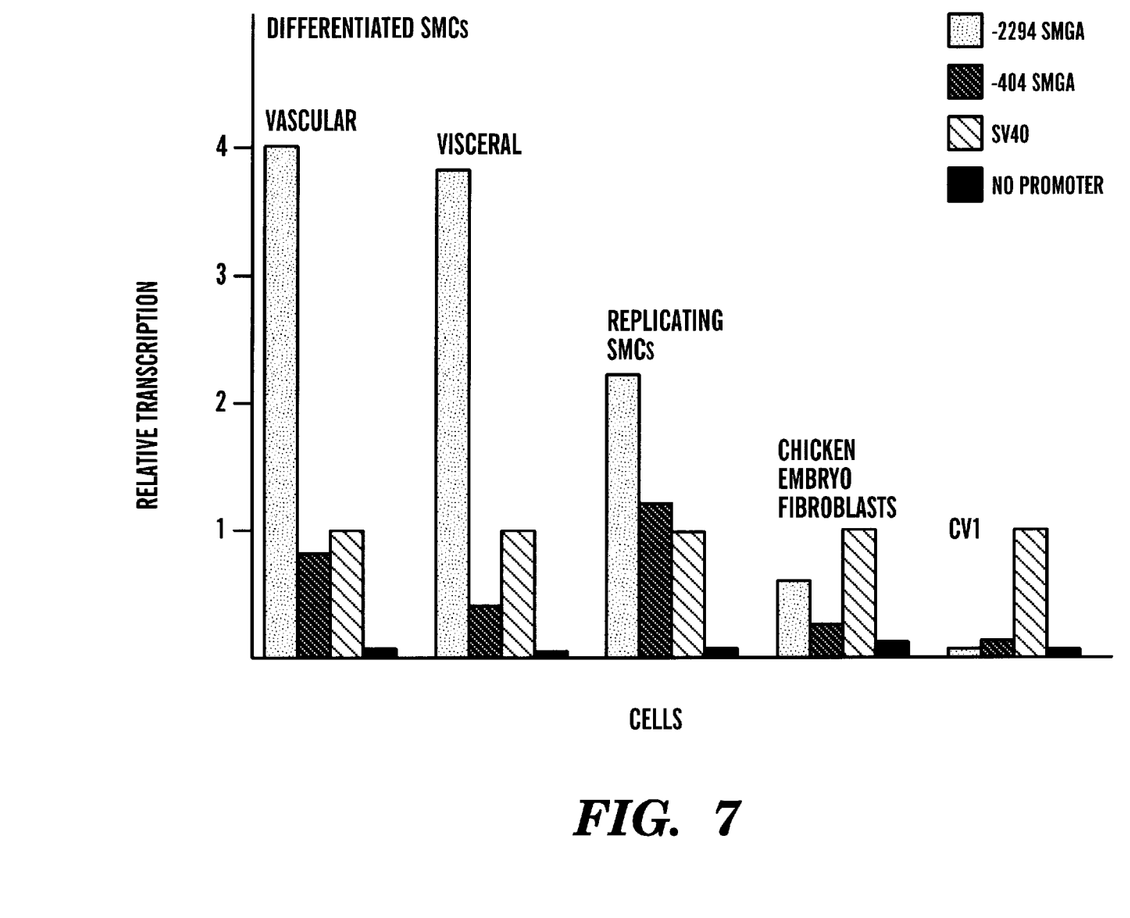
FIG. 7 illustrates the preferential expression of the SMGA promoter in differentiated SMCs.

A series of promoter constructs containing various lengths of the chicken SMGA promoter upstream of either a CAT or luciferase reporter gene were created, as well as plasmids containing either no promoter or the SV40 early promoter/enhancer as negative and positive controls, respectively (FIGS. 4–6). By transfecting cells with CAT or luciferase reporter constructs, the transcriptional activity of the SMGA promoter was analyzed. When the full length or truncated SMGA promoter was used, maximal expression of the reporter was observed in differentiated and replicating smooth muscle cells, whereas less than 10% of these levels of expression were observed in either fibroblasts or CV1 epithelial cells (FIG. 7). It should be pointed out that nearly identical levels of expression were detected in visceral and vascular smooth muscle cells (FIG. 7). In contrast, expression of the SV40 promoter/enhancer constructs was roughly equivalent in all cell types tested.

EXAMPLE II

Cell specific DNA nuclear import in smooth muscle cells.

Figure 8:
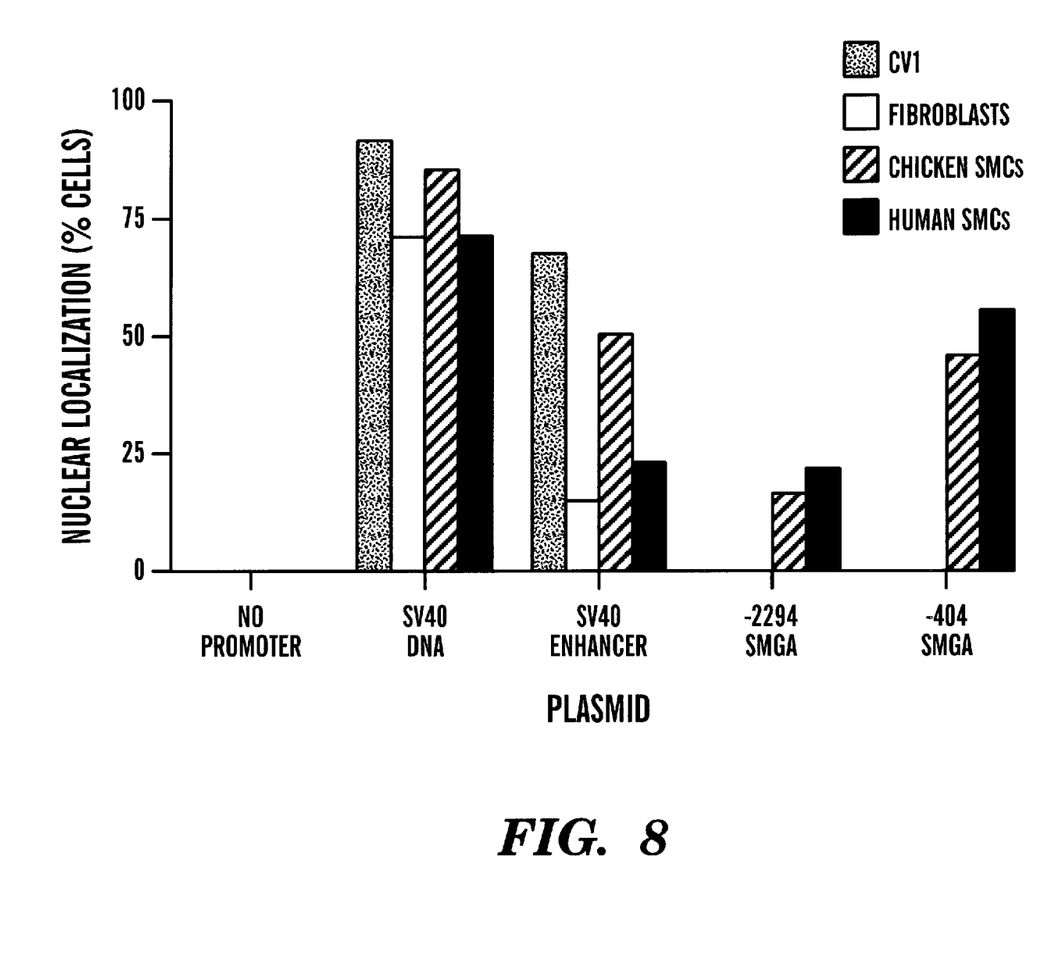
FIG. 8 illustrates the cell-specific nuclear import of the SMGA promoter.

The nuclear import of plasmid DNA is sequence specific. While SV40 DNA is imported into the nuclei of non-dividing cells, the bacterial plasmid pBR322 DNA remains cytoplasmic. However, when a DNA sequence from SV40 as small as 80 bp containing portions of the early promoter/enhancer is cloned into pBR322, the hybrid plasmid is now able to enter the nucleus (Dean 1997). Primary cultures of non-transformed smooth muscle cells from chicken viscera and human vasculature were able to display this sequence specific nuclear import of plasmid DNA. As FIG. 8 clearly demonstrates, both types of smooth muscle cells are able to transport SV40 DNA and a pCAT plasmid containing the SV40 promoter/enhancer into their nuclei, while a plasmid lacking the SV40 sequences (pCAT-basic, denoted "no promoter") is unable to localize to the nucleus. Virtually identical results are seen in chicken embryo fibroblasts and CV1 cells (FIG. 8).

DNA nuclear import can also be made cell-specific. The SMGA promoter constructs were microinjected into the cytoplasm of CV1, chicken embryo fibroblasts, non-dividing differentiated chicken smooth muscle cells, and non-dividing human smooth muscle cells, and the nuclear localization was measured by in situ hybridization 8 hours after injection (FIG. 8). Neither pCAT-2294 or pCAT-404 were imported into the nuclei of CV1 cells or chicken embryo fibroblasts; 100% of the injected DNA remained in the cytoplasm. In contrast, plasmids containing two different lengths of the SMGA promoter were imported into the nuclei of differentiated chicken and human smooth muscle cells only. In the case of the 404 bp construct, DNA nuclear import occurred at a frequency almost as high as that of the SV40 promoter/enhancer-containing construct. This is the first demonstration of cell-specific nuclear import of plasmid DNA and supports the model for plasmid DNA nuclear import.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

Graessman, M., and Graessman, A., in *Microinjection and organelle transplantation techniques: methods and applications*, J. E. Celis, et al., Editors, Academic Press, London, pp. 3–37 (1986).

TABLE 1

Examples of tissue-specific genes and some of the transcription factors responsible.

| Promoter | Transcription Factor | Tissue/cell specificity | Reference |
|---|---|---|---|
| insulin gene promoter | PDX-1, NeuroD/beta-2 | islet β-cells of the pancreas | Madsen et al. 1997 |
| $P450_{11\beta}$ promoter | Ad4BP | Steroidogenic cells (adrenal gland, testis, ovary, placenta, brain) | Morohashi et al. 1995 |
| immunoglobulin heavy and light chain promoters | Oct-2, OCA-B1 | lymphoid cells: B and T cells | Wirth et al. 1995 |
| somatotropin and prolactin promoters | Pit-1 | pituitary cells (somatotropes, lactotropes, thyrotropes) | Pellegrini-Bouiller et al. 1997 |
| transthyretin promoter | HNF4, HNF3β, HNF1, CBPα | liver cells | Cereghini 1996 |
| chicken cardiac actin proximal promoter element | serum response factor (SRF), cardiac myocyte factor HF1a, myogenic determination factor (MDF) | cardiac myocytes | Moss et al. 1994 |
| cardiac troponin proximal promoter element | SRF, TEF-1 | cardiac myocytes | Larkin et al. 1996 |
| T cell receptor promoter | T cell factor 1 (TCF-1), GATA-3 | T cells | Geise et al. 1995 |
| human CD2 downstream element | GATA-3, TCF-1, CBF | T cells | Wotton et al. 1995 |
| αA-crystallin gene | upstream stimulating factor (USF), αA-CRYBP1 | lens cells of the eye | Sax et al. 1997 |
| myelin basic protein promoter and proteolipid protein promoter | Gtx, myelin transcription factor I (MyT1) | oligodendrocytes | Awatramani et al. 1997 |
| surfactant protein B promoter | Sp1, Sp3, and TTF-1 and HNF-3α | alveolar type II epithelial cells and bronchiolar epithelial cells (Clara cells) | Margana and Boggaram 1997 |

REFERENCES

Allen, R. E., et al., J Cell Physiol 165:307–312 (1995).
Awatramani, R., et al., J Neurosci 17:6657–6668 (1997).
Baru, M., et al., Gene 161(2):143–150 (1995).
Berns, K. I. and C. Giraud, Ann NY Acad Sci 772:95–104 (1995).
Betz, A. L., et al., J Cereb Blood Flow Metab 15(4):547-551 (1995).
Brownlee, G. G., Br Med Bull 51(1):91–105 (1995).
Cambell, G. R., et al., J Anat 117:295–312 (1974).
Cereghini, S., FASEB J 10:267–282 (1996).
Datta, S., Development 121:1173–1182 (1995).
Dean, D. A., Exp Cell Res 230:293–302 (1997).
Dean, D. A., and Kasamatsu, H., J Biol Chem 269:4910–4916 (1994).
Dean, D. A., et al., J Virol 69:1115–1121 (1995).
DeLucia, A. L., et al., J Virol 57:138–144 (1986).
Dowty, M. E., et al., Proc Natl Acad Sci USA 92:4572–4576 (1995).
Ekhterae, D. and J. C. Stanley, J Vasc Surg 21(6):953–962 (1995).
Geise, K., et al., Genes Dev 9:995–1008 (1995).
Hayward, L. J., and Schwartz, R. J., J Cell Biol 102:1485–1493 (1986).
Herring, B., and Smith, A., Am J Physiol 270:C1656 (1996).
Hirt, B., J Mol Biol 26:365–369 (1967).
Johnson, C. V., et al., Meth Cell Biol 35:73–99 (1991).
Kallmeier, R., et al., J Biol Chem 270:30949–30957 (1995).
Kerr, W. G., and Mule, J. J., J Leukocyte Biol 56:210–214 (1994).
Knowles, M. R., et al., N Engl J Med 333(13):823–831 (1995).
Kojima, H., et al., Biochem Biophys Res Commun 212(2):712–717 (1995).
Kovacs, A. M., and Zimmer, W. E., Cell Motil Cytoskeleton 24:67–81 (1993).
Langan, T. J. and M. C. Slater, Brain Res 548:9–17 (1991).
Larkin, S., et al., Mol Cell Biol 16:3742–3755 (1996). Li, L., et al., J Cell Biol 132:849–859 (1996).
Madsen, O. D., et al., Horm Metab Res 29:265–270 (1997).
Mansouri, A., et al., J Cell Sci Suppl. 18:35–42 (1994).
Margana, R. K., and Boggaram, V., J Biol Chem 272:3083–3090 (1997).
Miller, L. K., Bioessays 11:91–95 (1989).
Miwa, T., et al., Mol Cell Biol 11:3296–3306 (1991).

Morohashi, K., et al., J Steroid Biochem Molec Biol 53:81–88 (1995).
Moser, M., et al., Development 121:2779–2788 (1995).
Moss, J. B., et al., J Biol Chem 269:12731–12740 (1994).
Nigg, E. A., Nature 386:779–787 (1997).
Orlic, D., et al., Blood 80:245a (1992).
Osborne, W. R., et al., Proc Natl Acad Sci USA 92(17):8055–8058 (1995).
Pellegrini-Bouiller, I., et al., Horm Res 47:251–258 (1997).
Phaneuf, D., et al., Biochem Biophys Res Comm 208(3):957–963 (1995).
Ponchio, L., et al., Blood 86:3314–3321 (1995).
Porth, C. M., *Pathophysiology: Concepts of altered health states*, 4th ed., JB Lippincott Co., Philadelphia, Pa., pp 72–74 (1994).
Rowland, R. T., et al., Ann Thorac Surg 60(3):721–728 (1995).
Samaha, F., et al., J Biol Chem 271:395–403 (1996).
Sambrook et al., *Molecular Cloning: A Laboratory Manual*, 2d Edition, Cold Spring Harbor Laboratory Press, Cold Spring Harbor, N.Y. (1989).
Sax, C. M., et al., Gene 185:209–216 (1997).
Scanlon, K. J., et al., FASEB J 9:1288–1296 (1995).
Seshadri, T. and J. Campisi, Exp Gerontol 24:515–522 (1989).
Shimizu, R. T., et al., J Biol Chem 270:7631–7643 (1995).
Stamatoyannopoulos, J. A. and A. W. Nienhuis, in *The Molecular Basis of Blood Diseases*, 2d Edition, Stamatoyannopoulos et al., eds., WB Saunders Co., Philadelphia Pa., pp. 107–156 (1994).
Stevenson, S. C., et al., Arterioscler Thromb Vasc Biol 15(4):479–484 (1995).
Sullenger, B. A. and T. R. Cech, Nature 371:619–622 (1994).
Szucsick, J., and Lessard, J., Genomics 28:154–162 (1995).
Tooze, J., *Molecular biology of tumor viruses*, 2d edition, Cold Spring Harbor Laboratory Press, Cold Spring Harbor, N.Y. (1980).
Treisman, R., Curr Opin Genet Dev 4:96–101 (1994).
Vallejos, et al., Genetics 112:93–105 (1986).
Vaulont, S., et al., Transgenic Res 4(4):247–255 (1995).
Vick, R. S., et al., J Neurosci Res 33:75–81 (1992).
Vrionis, F. D., et al., J Neurosurg 83(4):698–704 (1995).
Walther, C., and Gruss, P., Development 113:1435–1449 (1991).
Wirth, T., et al., Immunobiol 193:161–170 (1995).
Wotton, D., et al., J Biol Chem 270:7515–7522 (1995).
Young, J. C., et al., Blood 87:545–556 (1996).
Zimmer, W. E., et al., Dev Biol 175:399 (1996).

---

What is claimed is:

1. A nuclear targeting molecule having a nucleic acid sequence as shown in SEQ ID NO:1 or SEQ ID NO:2.

2. A plasmid for targeting an exogenous DNA molecule into nuclei of smooth muscle cells, the plasmid comprising:
   a nuclear targeting molecule having a first nucleic acid sequence as shown in SEQ ID NO:1 or SEQ ID NO:2, the first nucleic acid sequence including a binding site for a transcription factor, the transcription factor being unique to smooth muscle cells; and
   an exogenous DNA to be targeted to the nuclei of smooth muscle cells.

3. The plasmid of claim 2 wherein the plasmid further comprises nucleic acid encoding a selection marker.

4. The plasmid of claim 2 wherein the plasmid further comprises a bacterial origin of replication.

5. The plasmid of claim 2 wherein the plasmid further comprises a promoter, expression of the exogenous DNA molecule to be targeted to the nuclei being under control of the promoter.

6. The plasmid of claim 2 wherein the plasmid further comprises a second nucleic acid sequence to direct integration of the exogenous DNA molecule into the genome of the smooth muscle cells.

7. The plasmid of claim 6 wherein the second nucleic acid sequence to direct integration is a viral integration sequence.

8. The plasmid of claim 2 wherein the plasmid further comprises unique restriction sites for insertion of additional nucleic acid sequences.

9. The plasmid of claim 8 wherein the unique restriction sites are provided by a polylinker.

10. An isolated host cell comprising the plasmid of claim 2.

11. The isolated host cell of claim 10 wherein the isolated host cell is a non-dividing cell.

12. The isolated host cell of claim 11 wherein the non-dividing cell is a quiescent cell.

13. The isolated host cell of claim 11 wherein the non-dividing cell is a terminally differentiated cell.

14. A method of targeting an exogenous DNA into nuclei of smooth muscle cells, the method comprising:
   providing a plasmid for targeting an exogenous DNA into nuclei of smooth muscle cells, the plasmid comprising a nuclear targeting molecule having a nucleic acid sequence as shown in SEQ ID NO:1 or SEQ ID NO:2, the nucleic acid sequence including a binding site for a transcription factor, the transcription factor being unique to smooth muscle cells, and the plasmid further comprising an exogenous DNA to be targeted to the nuclei of smooth muscle cells; and
   introducing the plasmid into the cytoplasm of smooth muscle cells, wherein the nuclear targeting molecule targets the exogenous DNA into the nuclei of the smooth muscle cells.

15. The method of claim 14 wherein the smooth muscle cells are non-dividing cells.

16. The method of claim 15 wherein the non-dividing cells are quiescent cells.

17. The method of claim 15 wherein the non-dividing cells are terminally differentiated cells.

* * * * *